(12) United States Patent
Butler (10) Patent No.: US 8,361,766 B2
(45) Date of Patent: Jan. 29, 2013

(54) CONTINUOUS SINGLE VESSEL BUTANOL SYNTHESIS BY FERMENTATION

(76) Inventor: Eugene Butler, Brookings, SD (US)

( * ) Notice: Subject to any disclaimer, the term of this patent is extended or adjusted under 35 U.S.C. 154(b) by 0 days.

(21) Appl. No.: 12/942,957

(22) Filed: Nov. 9, 2010

(65) Prior Publication Data

US 2011/0143407 A1    Jun. 16, 2011

Related U.S. Application Data (60) Division of application No. 12/393,986, filed on Feb. 26, 2009, now Pat. No. 7,833,778, which is a continuation-in-part of application No. 12/391,026, filed on Feb. 23, 2009, now abandoned.

(51) Int. Cl.
*C12P 7/16* (2006.01)
(52) U.S. Cl. ............ 435/160; 435/166; 435/252.7
(58) Field of Classification Search .............. None
See application file for complete search history.

(56) References Cited

U.S. PATENT DOCUMENTS

| | | | |
|---|---|---|---|
| 4,359,533 A * | 11/1982 | Wilke et al. | ............ 435/161 |
| 6,358,717 B1 | 3/2002 | Blaschek | |
| 2005/0089979 A1 | 4/2005 | Ezeji et al. | |
| 2008/0248540 A1 | 10/2008 | Yang | |
| 2008/0274524 A1 | 11/2008 | Bramucci | |

FOREIGN PATENT DOCUMENTS

WO    2008076749    1/2008

OTHER PUBLICATIONS

Park et al., Separation and Purification Metods, 21(2), 127-174, 1992.*
Search Report and Written Opinion of PCT Ser No. US09/35327.
Klijn et al., Identification . . . PCR Amplification, App Environ Micro 61(8)2919-2924, 1995.
Keis et al., Emended descriptions . . . sp. nov, Int J Syst Evol Micro 51, 2095-2103, 2001.
Qureshi & Blaschek, Evaluation . . . processing, Bioproc Biosyst Engineer 24, 219-226, 2001.
Kanouni et al., Evaluation . . . carbonate, World J Micro Biotech 14, 431-435, 1998.
Park et al., Acetone . . . reactor, Biotech Bioengineer, 34(1), 2004, Abstract only.

* cited by examiner

*Primary Examiner* — Allison Ford
*Assistant Examiner* — Yvonne Pyla
(74) *Attorney, Agent, or Firm* — MDIP LLC (57) ABSTRACT

The present invention describes a method for producing butanol by fermentation of carbohydrates using mixed populations of acidogenic-phase cells and solventogenic-phase cells of *Clostridium* in a solitary vessel. The present system as described does not require intermittent adjustment of pH or venting of headspace gases. The method provides a process for removal of the butanol product which does not irreversibly harm the cells and conditions are described where such cells may resume butanol synthesis in the same solitary vessel. The invention also describes compositions and biologically pure cultures which comprise the *Clostridium* cells as disclosed.

17 Claims, 8 Drawing Sheets

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Primer, Clostridium Species 16S rRNA Conserved
      Region 41-60

<400> SEQUENCE: 1
gcggcgtgcc taatacatgc                                              20

<210> SEQ ID NO 2
<211> LENGTH: 20
<212> TYPE: DNA
<213> ORGANISM: Artificial Sequence
<220> FEATURE:
<223> OTHER INFORMATION: Primer, Clostridium species 16S rRNA Conserved
      Region 1094-1114

<400> SEQUENCE: 2
gggttgcgct cgttgcggga                                              20

<210> SEQ ID NO 3
<211> LENGTH: 20
<212> TYPE: DNA
<213> ORGANISM: Artificial Sequence
<220> FEATURE:
<223> OTHER INFORMATION: Primer, Clostridium species 16S rRNA Conserved
      Region 361-380
```

<400> SEQUENCE: 3
ggaatcttcc acaatgggcg            20

<210> SEQ ID NO 4
<211> LENGTH: 24
<212> TYPE: DNA
<213> ORGANISM: Artificial Sequence
<220> FEATURE:
<223> OTHER INFORMATION: Primer, Clostridium acetobutylicum 1000-1050 V6
      Region

<400> SEQUENCE: 4
ggacttcatc cattacggac taac            24

<210> SEQ ID NO 5
<211> LENGTH: 24
<212> TYPE: DNA
<213> ORGANISM: Artificial Sequence
<220> FEATURE:
<223> OTHER INFORMATION: Primer, Clostridium beijerinkii 1000-1050 V6
      Region

<400> SEQUENCE: 5
cttccccgat taagggtaat tcag            24

<210> SEQ ID NO 6
<211> LENGTH: 24
<212> TYPE: DNA
<213> ORGANISM: Artificial Sequence
<220> FEATURE:
<223> OTHER INFORMATION: Primer, Clostridium butyricum 1000-1050 V6
      Region

<400> SEQUENCE: 6
gtggcttgct ccattacaga gtaa 24

<210> SEQ ID NO 7
<211> LENGTH: 22
<212> TYPE: DNA
<213> ORGANISM: Artificial Sequence
<220> FEATURE:
<223> OTHER INFORMATION: Primer, Clostridium tyrobutyricum 1000-1050 V6
Region

<400> SEQUENCE: 7
cgcctatctc taggttattc ag 22

<210> SEQ ID NO 8
<211> LENGTH: 22
<212> TYPE: DNA
<213> ORGANISM: Artificial Sequence
<220> FEATURE:
<223> OTHER INFORMATION: Primer, Clostridium sporogenes 1000-1050 V6
Region

<400> SEQUENCE: 8
cacctatctc taggctatgc aa 22

CONTINUOUS SINGLE VESSEL BUTANOL SYNTHESIS BY FERMENTATION

CROSS REFERENCE TO RELATED APPLICATION

This application is a Continuation-in-Part of U.S. Ser. No. 12/391,026, filed on Feb. 23, 2009, now abandoned, the disclosure of which is hereby incorporated-by-reference in its entirety.

BACKGROUND OF THE INVENTION

1. Field of the Invention

The present invention relates generally to the production of butanol by fermentation, and specifically to single vessel butanol production via generation of a micro-environment to maintain coincident subpopulations of acidogenic- and solventogenic-phase cells.

2. Background Information

Butanol (n-butanol or n-butyl alcohol) may be produced by the fermentation of carbohydrates which break down into products such as sugars containing five and six carbon atoms (e.g., glucose). This process was developed by Charles Weizmann during World War I (see, e.g., U.S. Pat. Nos. 1,315,585; 1,329,214; 1,437,697). Briefly, the Weizmann process comprises fermentation of a suitable feedstock in the presence of Clostridium acetobutylicum which convert the feedstock into a solvent mixture of acetone, butanol, and ethanol (ABE). In the solvent mixture, the ratio of butanol to acetone to ethanol is usually 6:3:1.

ABE fermentation is a biphasic process: during the first (acidogenic) phase, logarithmic growth is accompanied by acetic and butyric acid production which also causes a concomitant and necessary drop in pH. In the second (solventogenic) phase, growth ceases and the solvents are produced with the simultaneous consumption of the aforementioned acids, including the further consumption of the input feedstock. Hydrogen and carbon dioxide are continuously produced throughout the fermentation.

The resulting solvents are produced in dilute aqueous solutions, generally from about 1% to 2% by weight, so that their recovery in pure form involves their separation from large amounts of water. The expense of separation has been such that production of these chemicals by fermentation has not been able to compete with solvent production from petroleum-based sources. However, the concern for global warming, a desire to achieve energy independence, and the increase in prices of petrochemical-derived feedstocks have led to the revival of interest in processes which can convert renewable, unrefined materials into simple organic chemicals.

One problem associated with ABE fermentation by Clostridium microorganisms is butanol toxicity to the culture (i.e., the maximum tolerated butanol concentration is approximately 2%, irrespective of sugar concentration). Toxicity may be avoided by continuous removal of butanol during the process for maximum production of solvents. Various butanol removal systems, including adsorption, pervaporation, perstraction, reverse osmosis, liquid-liquid extraction, and gas stripping, have met with limited success. Further, all of the above methods increase production costs. Thus, there remains a need in the art for an improved process to generate solvents from these organisms.

SUMMARY OF THE INVENTION

The present invention describes a method for producing butanol by fermentation of carbohydrates via cells of the Clostridium genus, where a mixture of acidogenic-phase cells and solventogenic-phase cells are maintained in a single vessel. The present system does not require intermittent adjustment of pH or venting of headspace gases. The method as disclosed provides a process for removal of the butanol product which does not irreversibly harm the cells, where such cells may resume butanol synthesis when inhibitory concentrations of the solvent are no longer present. Further, the present invention includes compositions and biologically pure cultures which comprise Clostridium cells.

In one embodiment, a continuous process for the production of butanol is disclosed including contacting a culture of Clostridium cells and a buffering agent with a carbohydrate containing substrate in a first vessel, culturing the cells at an optimum temperature until an inhibitory concentration of butanol is attained, decreasing the pressure in the first vessel until vigorous boiling commences, transferring a butanol containing azeotrope from the first vessel to a second collection vessel as a condensate, flushing the first vessel with a purging fluid, and continuously repeating the above steps. In a related aspect, flushing is a function of condensation collection volume, where the flushing is initiated when the condensation collection volume is about 4% to 5% of culture volume.

In another aspect, the pressure is decreased from about 760 mm Hg to about 20 mm Hg to 30 mm Hg. In another aspect, the carbohydrate containing substrate is replenished when solvent yield is about 35% to 40% (wt/wt) of assimilable carbohydrate in the substrate.

In one aspect, the cells include, but are not limited to, C. beijerinkii, C. acetobutylicum, C. aurantibutyricum, C. tetranomorphum, and C. thermocellum. In a related aspect, the Clostridium beijerinkii is NRRL No. B-50244.

In another embodiment, a continuous process for the production of butanol is disclosed including contacting a single culture of Clostridium cells and a buffering agent with a carbohydrate containing substrate in a first vessel, culturing the cells at an optimum temperature until an inhibitory concentration of butanol is attained, increasing the temperature of the culture about 6° C. to 11° C. above the optimum temperature and decreasing the pressure in the first vessel from about 760 mm Hg until vigorous boiling commences, transferring a butanol containing azeotrope from the first vessel to a second vessel as a condensate, flushing the first vessel with purging fluid and cooling the culture to the optimal temperature for butanol synthesis as a function of condensation collection volume, and continuously repeating the above steps.

In one aspect, the carbohydrate containing substrate is replenished when solvent yield is about 35% to 40% (wt/wt) of the assimilable carbohydrate. In another aspect, the culture comprises a mixture of cells in the acidogenic and solventogenic phase. In a related aspect, the Clostridium cells are C. beijerinkii. In another aspect, the purging fluid is $N_2$ gas.

In one aspect, the optimum temperature is about 33° C. to 37° C. In another aspect, the temperature is increased to about 43° C. to 44° C. In a further aspect, the pressure is decreased to about 110 mm Hg to 100 mm Hg.

In one aspect, the inhibitory concentration of butanol is about 0.9% to 2.0%. In a related aspect, the inhibitory concentration of butanol is about 1.3%.

In another aspect, the buffering agent comprises a biological source of calcium carbonate, including cuttlebone and oyster shell. In one aspect, the method further includes contacting the cells with a molecular scaffold. In a related aspect, the molecular scaffold includes fragments of sponge, where the sponge contains calcium carbonate, silica spicules, or cellulose.

In one aspect, the process results in a butanol yield of between about 35 to 40% (w/w) from fermentable carbohydrate, including a process yield of butanol of about 20 g/L per cycle. In another aspect, the process produces a headspace gas mixture containing about 40 to 50% $H_2$, about 40 to 50% $CO_2$, and 0 to 20% $N_2$. In a related aspect, the headspace gas contains 43% $H_2$, 43% $CO_2$, and 14% $N_2$.

In another embodiment, a composition is disclosed including a mixed population of acidogenic-phase and solventogenic-phase cells of the genus *Clostridium* and a buffering agent including a biological calcium carbonate source. In one aspect, the biological calcium carbonate source includes cuttlebone fragments and oyster shell fragments. In another aspect, the buffering agent is an inorganic calcium carbonate source.

In another aspect, the composition further contains a cellulosic biomass including stalks, leaves, husks, wood chips, sawdust, dead trees, tree branches, household garbage, paper products, black liquor, grasses or a combination thereof.

In one aspect, the cells are *Clostridium beijerinkii*. In a related aspect, the *Clostridium beijerinkii* is NRRL No. B-50244. In another aspect, the *Clostridium beijerinkii* is intercalated in a solid phase including natural sea sponge, cellulose sponge, calcium alginate beads, and polyacrylamide sheets.

In one embodiment, a biologically pure culture of *Clostridium beijerinkii* NRRL No. B-50244 is disclosed. In one aspect, the culture may continue to produce butanol at pH 6.0. In another aspect, the culture is embedded in a solid phase. In a related aspect, the solid phase includes natural sea sponge, cellulose sponge, *luffa* sponge, calcium alginate beads, mollusk shell fragments, cuttlefish bone fragments, and polyacrylamide sheets.

DETAILED DESCRIPTION OF THE INVENTION

Before the present compositions, methods, and methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "a cell" includes one or more cells, and/or compositions of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure.

As used herein, "a mixed population of acidogenic-phase and solventogenic-phase cells" means an assorted number of *Clostridium* cells containing a subpopulation of predominantly butyric and acetic acid producing cells and a subpopulation of predominantly acetone/butanol/ethanol (ABE) producing cells. Such strains include *C. beijerinkii*, *C. acetobutylicum*, *C. aurantibutyricum*, *C. tetranomorphum*, *C. thermocellum* and similar bacteria which convert carbohydrates, butyric acid and other acids into solvents such as butanol, acetone, ethanol or isopropanol. In some aspects, the sub-populations are from a single strain or multiple strains. In another aspect, cells usable in the processes as disclosed in the present invention may be naturally occurring or artificial (i.e., result from recombinant manipulation).

As used herein, "a biological calcium carbonate source" means that the supply of calcium carbonate is from the shell or skeletal material (or fragments thereof) of an animal. For example, the shell of an animal belonging to the phylum Mollusca would be a biological calcium carbonate source.

As used herein, "cellulosic biomass" means material composed of cellulose, hemicellulose and lignin, with smaller amounts of proteins, lipids (fats, waxes and oils) and ash. Such biomass contains assimilable carbohydrates (i.e., carbohydrate substrates). Examples of assimilable carbohydrates include, but are not limited to, sugars such as glucose, lactose, whey permeate, pentose sugars, starch, liquefied starch, enzyme-treated liquefied starch, maltodextrin, and corn steep liquor. In one aspect, such assimilable carbohydrates may be analyzed as dextrose equivalents (e.g., using an YSI analyzer after treatment of biomass with glucoamylase and α-amylase, see, e.g., U.S. Pat. No. 5,192,673 or by dinitro salicyclic acid, see, e.g., Tasun et al., Biotech Bio-eng (1970) 12:991-992).

As used herein, "solid phase" means a state of matter characterized by resistance to deformation and changes of volume. In one aspect, the solid phase may be porous or non-porous. In a related aspect, the porous solid phase may be colonized by the selected bacteria, where the colonized solid phase serves as an inoculate for new cultures. For example, the solid phase may be a 3-dimensional molecular scaffold, where such a scaffold provides a greater surface area for cell growth (e.g., a sponge). In a related aspect, "embedded" means that the cells are intercalated into the interstices of the solid phase.

As used herein, "purging fluid" means a liquid or gas for washing out other liquids or gases. For example, $CO_2$ and $N_2$ gases are purging fluids.

Bioproduced 1-butanol may be isolated from a fermentation medium using methods known in the art. For example, solids may be removed from the fermentation medium by centrifugation, filtration, decantation, or the like. Then, the 1-butanol may be isolated from the fermentation medium, which has been treated to remove solids, using methods such as distillation, liquid-liquid extraction, or membrane-based separation. Since 1-butanol forms a low boiling point, azeotropic mixture with water, distillation can only be used to separate the mixture up to its azeotropic composition. Generally distillation has been used in combination with another separation method to obtain separation around the azeotrope. Methods that may be used in combination with distillation to isolate and purify 1-butanol include, but are not limited to, decantation, liquid-liquid extraction, adsorption, and membrane-based techniques.

The 1-butanol-water mixture forms a heterogeneous azeotrope so that distillation may be used in combination with decantation to isolate and purify the 1-butanol. In one method, the 1-butanol containing fermentation broth is distilled to near the azeotropic composition. Then, the azeotropic mixture is condensed, and the 1-butanol is separated from the fermentation medium by decantation. The decanted aqueous phase may be returned to the first distillation column as reflux. The 1-butanol-rich decanted organic phase may be further purified by distillation in a second distillation column.

1-butanol has also been isolated from a fermentation medium using liquid-liquid extraction in combination with distillation. In such a method, the 1-butanol is extracted from the fermentation broth using liquid-liquid extraction with a suitable solvent. The 1-butanol-containing organic phase is then distilled to separate the 1-butanol from the solvent.

Distillation in combination with adsorption may also be used to isolate 1-butanol from the fermentation medium. In such a method, the fermentation broth containing the 1-butanol is distilled to near the azeotropic composition and then the remaining water is removed by use of an adsorbent, such as molecular sieves (Aden et al., Lignocellulosic Biomass to Ethanol Process Design and Economics Utilizing Co-Current Dilute Acid Prehydrolysis and Enzymatic Hydrolysis for Corn Stover, Report NREL/TP-510-32438, National Renewable Energy Laboratory, June 2002).

Additionally, distillation in combination with pervaporation has been used to isolate and purify the 1-butanol from the fermentation medium. In this method, the fermentation broth containing the 1-butanol is distilled to near the azeotropic composition, and then the remaining water is removed by pervaporation through a hydrophilic membrane (Guo et al., J. Membr. Sci. 245, 199-210 (2004)).

In all of these distillation methods, the fermenting organism must be separated from the broth to be distilled, since temperatures typically used to distill the butanol-water azeotrope (e.g., about 93° C.) will irreversibly harm cells in the vegetative state. Therefore, in contrast to the present method, the distillation processes as recited above cannot be carried out in the same vessel as the active culture without destroying the cells.

Various processes have been implemented for in situ removal of butanol from productive cultures. Techniques examined include absorption, pervaporation, reverse osmosis, liquid-liquid extraction, and gas stripping. All of the above methods increase production expense significantly, and none are optimal. The membrane based systems that display high selectivity for butanol are subject to fouling and clogging with both *C. acetobutylicum* and *C. beijerinkii*. Gas stripping may work well with modeled solutions from which one may wish to remove volatile components (see, e.g., U.S. Application No. 20050089979), but the vigorous bubbling of inert gas through the solution to be purged is contraindicated when, for example, cultures are to be left unperturbed for butanol production.

In the present invention, a process for the production of butanol is disclosed including contacting a single culture of *Clostridium* cells and a buffering agent with a carbohydrate-containing substrate in a first solitary vessel, culturing the cells at an optimum temperature until an inhibitory concentration of butanol is attained, and decreasing the pressure in the same solitary vessel until vigorous boiling commences, transferring a butanol-containing azeotrope from the first vessel to a second collection vessel as a condensate, flushing the first vessel with purging fluid as a function of condensation collection volume, where flushing is initiated when the volume of condensate collected is about 4 to 5% of the fermentation volume, and continuously repeating the above steps. Thus, distillation of the resulting butanol-water azeotrope is carried out in the same vessel as the active culture. Further, after distillation, the same culture may be used to resume butanol production.

In one aspect, the process produces at least 0.4 grams of butanol per gram of glucose or other sugars consumed including, but not limited to, lactose. In another aspect, the process achieves a maximum butanol yield of between about 80% to 90% from fermentable carbohydrate. In a further related aspect, the process yield of butanol is about 20 to 40 g/L.

In another aspect, the *Clostridium* cells are *C. beijerinkii*, *C. acetobutylicum*, *C. aurantibutyricum*, *C. thermocellum*, or *C. tetranomorphum*. In a related aspect, the cells are *C. beijerinkii* NRRL No. B-50244.

Generally, fermentation is allowed to proceed for at least about 36 h, however, fermentation may be allowed to proceed for 140 h or more. For the present invention, cell concentration is maintained at late log phase to stationary phase for continuous solvent production, where spent media and cells are replaced as necessary. Depending on the *Clostridium* strain used, the cells may be agitated or kept stationary. For example, when *C. beijerinkii* is used, the cultures are to be left unperturbed for butanol production.

For the present invention, feedstocks may be simple sugars, such as glucose, lactose (e.g., as contained in whey permeate), pentose sugars; complex sugars, such as starch, liquefied starch, enzyme-treated liquefied starch, maltodextrin, and corn steep liquor; or may comprise cellulosic biomass. Such feedstocks are delivered as solutions and/or suspensions in water. In one aspect, when a substrate solution is derived from feedstock containing cellulosic biomass, such biomass may be milled or micronized prior to fermentation. Milling reduces the size of the feedstock components containing the carbohydrates, thus, making the biomass easier to decompose by the selected bacterium. Sterilization may be used to kill background bacteria, allowing the bacterium of choice to flourish. Typically, carbohydrates/sugars are mixed with water and then sterilized as is common to many fermentation systems (see, e.g., U.S. Pat. No. 5,753,474). Again, carbohydrates making up the feedstock/sugars may be analyzed as dextrose equivalents (e.g., using an YSI analyzer after treatment of biomass with glucoamylase and α-amylase, see, e.g., U.S. Pat. No. 5,192,673 or by dinitro salicyclic acid, see, e.g., Tasun et al., Biotech Bio-eng (1970) 12:991-992).

In addition to the carbohydrate containing substrate, cells are contacted with nutrient media. Useful nutrient media include those known in the art, such as P2 and tryptone glucose yeast extract (TGY). Other nutrient media can be used. The nutrient media may optionally contain additives such as salt and/or trace minerals. In one aspect, the medium is Lactose Sporulation Medium (LSM), as defined in Table I.

TABLE I

LSM. (one liter)

| Component | Amount |
|---|---|
| $KH_2PO_4$ (anhydrous) | 0.75 g |
| $K_2HPO_4$ (anhydrous) | 0.70 g |
| $MgSO_4$ (Epsom salt) | 0.02 g |
| NaCl | 1.0 g |
| Cysteine | 0.5 g |
| Asparagine | 2.0 g |
| $(NH_4)_2SO_4$ | 2.0 g |
| Resazurin | 0.1 g |
| Hunter's Trace Elements Mix | 2X (2 ml of 1000 X Mix) |
| Lactose | 4% to 5% |
| Water | to 1 liter |

Hunter's Trace Element 1000× Mix (One Liter)

| | |
|---|---|
| $Na_2EDTA$ | 50 g |
| $ZnSO_4 \cdot 7H_2O$ | 22 g |
| $H_3BO_3$ | 11.4 g |
| $MnCl_2 \cdot 4H_2O$ | 5.06 g |
| $FeSO_4 \cdot 7H_2O$ | 4.99 g |
| $CoCl_2 \cdot 6H_2O$ | 1.61 g |
| $CuSO_4 \cdot 5H_2O$ | 1.57 g |
| $(NH_4)_6Mo_7O_{24} \cdot 4H_2O$ | 1.10 g |
| $H_2O$ | to one liter |

Generally, the solvent producing activity of a solventogenic *Clostridium* culture ceases if the pH is allowed to fall to 4.5 or below. For the present invention, the starting pH of the weakly-buffered growth media is at about pH 6.5 to 7.0 to foster the acidogenic phase (i.e., generation of butyric acid). The pH of the solution is then allowed to fall to trigger a shift from the acidogenic phase to the solventogenic/butanol synthesis phase. In one aspect, the pH during butanol generation is about 4.8 to 5.0, about 5.0 to 5.3, about 5.3 to 5.5, or about 5.5 to 6.0.

pH may be maintained using various salts, including, but not limited to, calcium carbonate, to prevent the culture pH from falling below 4.8 to 6.0. For the present invention, to maintain coincident subpopulations of acidogenic- and solventogenic-phase cells in a culture, sources of buffering salts that have a large gradient of buffering capacity are useful (i.e., exhibit slower release of counter ions). In one aspect, salts crystals are substituted by biological sources containing the same salt. For example, calcium carbonate crystals may be substituted by shells or skeletal material of mollusks, including, but not limited to, cuttlebone or oyster shell fragments. In addition, solid phases containing 3-dimensional scaffolds may be used to provide increased surface area for bacterial growth. In one aspect, fragments of sponge are included (e.g., but not limited to, natural sea sponge or cellulose sponge), which are colonized by the bacteria. In a related aspect, the sponge fragments that have been so colonized serve as inoculates for new cultures to initiate solvent production.

It is well known in the art that butanol at concentrations of about 1.0% are toxic to most *Clostridium* cultures (see, e.g., Hermann et al., App Env Microbiol (1985) 50(5):1238-1243), which can limit batch-wise production of the solvent by fermentation. In one aspect, when the butanol concentration reaches about 0.9 to 1.3%, the temperature of the culture may be increased about 6° C. to 11° C. above the optimal range for butanol production, and the pressure above the culture may be reduced to initiate boiling of the resultant azeotropic mixture of butanol and water. In one aspect, the optimal temperature for vegetative growth is between about 33° C. to 35° C., about 35° C. to 36° C., or 36° C. to 37° C. In related aspect, the temperature is raised to about 41° C. to 42° C., to about 42° C. to 43° C., to about 43° C. to 44° C., to about 44° C. to 46° C. In one aspect, the temperature is 46.5° C. In another aspect, the pressure may be reduced from about 760 mm Hg to about 110 mm Hg to 106 mm Hg, about 106 mm Hg to 105 mm Hg, or about 105 mm Hg to 100 mm Hg. By combining increased temperature above the optimal temperature for vegetative cell growth and reducing the pressure such that the vapor pressure of azeotrope is equal to the pressure above the culture, vacuum distillation may be achieved in the culture vessel without irreparably harming the cells.

In another aspect, the temperature may be maintained at the optimal temperature for butanol production and the pressure may be reduced from about 760 mm Hg to about 50 mm Hg to 40 mm Hg, to about 40 mm Hg to 30 mm Hg, or to about 30 mm Hg to about 20 mm Hg. Thus, by reducing the pressure sufficiently, such that the vapor pressure of azeotrope is equal to the pressure above the culture, again vacuum distillation may be achieved in the culture vessel without irreparably harming the cell.

For solvents generated using the processes as disclosed, the butanol may be separated from the active culture through vacuum distillation, where the resulting butanol-water azeotrope is captured as a condensate. Further, because the cells are not irreparably harmed by the process as disclosed, butanol may be generated, separated, and solvent production resumed in a single vessel.

Figure 1:
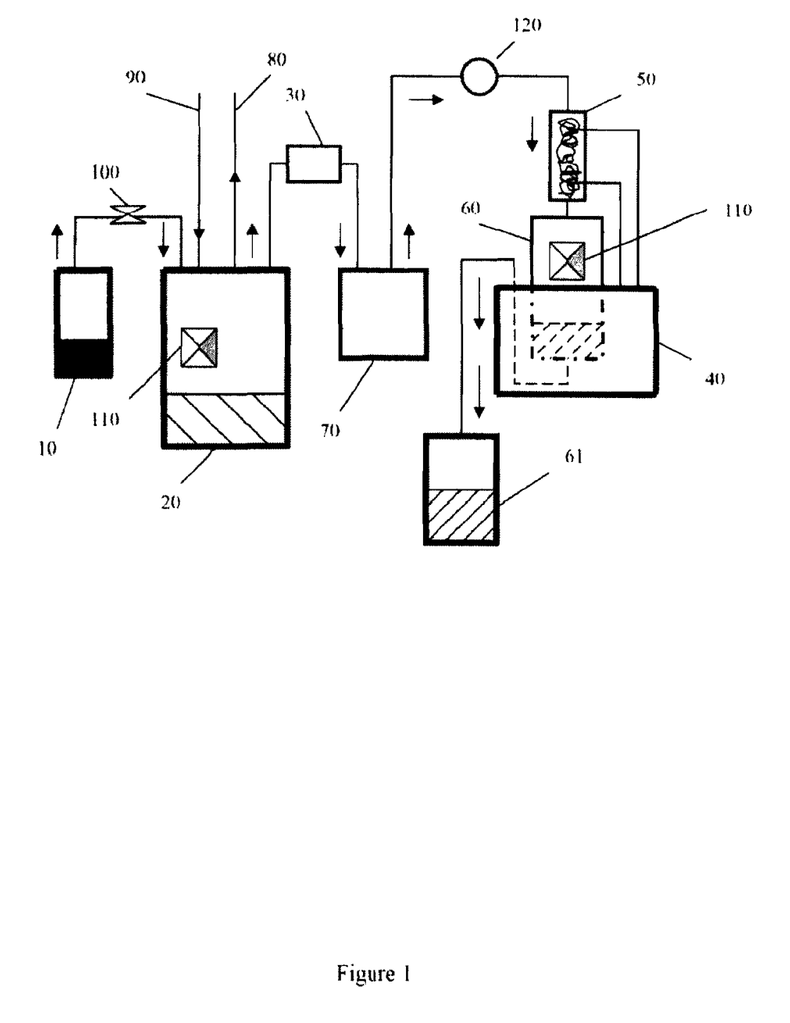
FIG. 1 shows a schematic of an apparatus useful for continuous single vessel butanol production.

A schematic diagram of the processes described herein is shown in FIG. 1. In this embodiment, the carbohydrate containing source may be fed into a first (culture) vessel (20) from a feed tank (10). The first vessel (20) may contain P2 or other nutrient medium and an appropriate carbohydrate source (e.g., but not limited to, glucose, lactose, pentose sugars; complex sugars, such as starch, liquefied starch, enzyme-treated liquefied starch, maltodextrin, and corn steep liquor; or cellulosic biomass derived carbohydrates, and the like), which is inoculated with selected *Clostridium* cells. The vapors generated by vacuum distillation as disclosed may be cycled through the system using an appropriate pump (30), and may be condensed using a cooling machine (40) and a condenser (50), where the solvents are collected in a separate vessel (60). The solvent-containing condensate may be transferred to one or more separate vessels (61) for further manipulation or storage. Additional components for the process may include, but are not limited to, one or more antifoam vessels (70), one or more bleeder lines (80), one or more input lines, (90), one or more valves (100), one or more monitoring devices (110) (e.g., to monitor cell concentration, butanol concentration, condensation rate, temperature and the like), and one or more gauges (120) (e.g., pressure/vacuum gauges) for continuous or batch operation. In one aspect, the one or more lines (80,90) and one or more valves (100) may be under electrical, mechanical, or manual control, or a combination thereof.

During continuous operation of the presently disclosed processes, when the volume of the condensate collected reaches about 4% to 5% of the original culture volume, the culture vessel (20) may be flushed with a purging fluid (e.g., nitrogen gas), and where appropriate, the temperature may be returned to optimal. Further, for continuous operation, when solvent yields are about 35% to 40% (by weight) of assimilable carbohydrate (which indicates that the culture has consumed most of the available carbohydrate substrate) more substrate is added as a solution at that time point to replace the volume of liquid distilled from the culture vessel (20).

To produce >99% butanol from the condensate as disclosed, water may be separated from the solvent by means well known in the art (e.g., adsorption, absorption, pervaporation, perstraction, reverse osmosis, liquid-liquid extraction, and gas stripping). Solvents from fermentation may be analyzed by methods well known in the art, including, but not limited to, gas chromatography.

In another embodiment, a composition is disclosed including a mixed population of acidogenic-phase and solventogenic-phase cells of the genus *Clostridium* and a buffering agent including a biological calcium carbonate source. In one aspect, the biological calcium carbonate source includes cuttlebone fragments or oyster shell fragments.

In one aspect, *C. beijerinkii* may be used for the present invention. The culture may be inoculated into LSM medium and incubated anaerobically for at least 36 h at about 33° C. to 37° C.

In a related aspect, the *C. beijerinkii* is NRRL No. B-50244. *C. beijerinkii* NRRL No. B-50244 was deposited with the Agricultural Research Culture Collection (NRRL), Peoria, Ill., under the terms of the Budapest Treaty on Feb. 12, 2009. In a further related aspect, the *C. beijerinkii* NRRL No. B-50244 produces butanol in the pH range of about 5.0 to 5.5. Moreover, the deposited strain may continue to produce butanol at pH 6.0. In another aspect, the *C. beijerinkii* is embedded in a solid phase including natural sea sponge, cellulose sponge, luffa sponge, calcium alginate beads, and polyacrylamide sheets.

In one embodiment, a biologically pure culture of *Clostridium beijerinkii* NRRL No. B-50244 is disclosed. In one aspect, the culture is embedded in a solid phase. In a related aspect, the solid phase includes natural sea sponge, cellulose sponge, calcium alginate beads, and polyacrylamide sheets.

The process described herein can be easily scaled up to a larger scale by suitable selection of reactor size, condenser size and other apparatus modifications, as known to one of ordinary skill in the art. The *Clostridium* cell concentration, carbohydrate concentration, and other parameters are adjusted to provide a continuous process, using the description herein, as well as the knowledge of one of ordinary skill in the art.

The operation of the processes described herein can be automated using, for example, a microprocessor system. For example, the system can monitor total solvent concentration, compare the total solvent concentration to a predetermined value, and remove a portion of the culture when the concentration is greater than a predetermined value or add an inoculum when the concentration is lower than a predetermined value. The system can also add water or other additives to maintain a predetermined volume in the fermentor/culture vessel. The system can monitor the carbohydrate concentration, compare the carbohydrate concentration to a predetermined value, and if the carbohydrate concentration is lower than the predetermined value, add carbohydrate solution. Alternatively, the system can monitor the butanol concentration of the fermentation broth, compare the butanol concentration to a predetermined value, and if the butanol concentration is greater than the predetermined value, add carbohydrate solution. In a related aspect, if the butanol concentration is greater than the predetermined value, the system may increase the temperature of the culture and decrease the pressure above the culture to distill and separate the butanol from the fermentation broth.

The system can monitor the rate of condensate collection from the fermentation broth, and compare the collection rate to a predetermined value, and if the collection rate is lower than the predetermined value, the culture vessel may be purged with $N_2$ gas and the temperature cooled (where appropriate) to resume butanol production.

Figure 6:
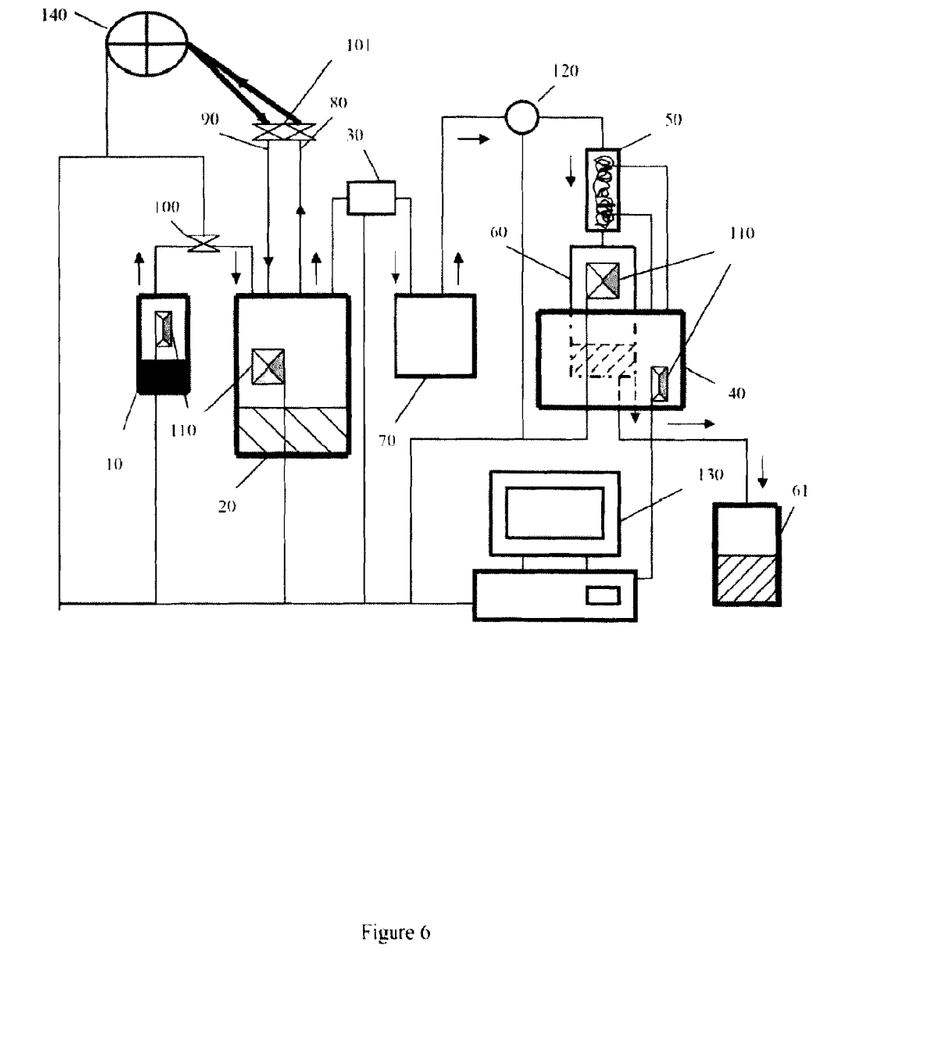
FIG. 6 shows a schematic of an automated embodiment of the apparatus as shown in FIG. 1.

Such an automated system is shown in FIG. 6. In this embodiment, the main components (10), (20), (30), (40), (50), (60), (61), (70), (80), (90), (100), (110), and (120) are the same as those shown in FIG. 1, and may further include a microprocessor (130) and a vent/reservoir (140). The vent/reservoir (140) is electrically coupled to a valve (101), which valve (101) is configured to be in fluid and mechanical communication with the vent/reservoir (140), bleeder (80) and input (90) lines, as well as in functional communication with the microprocessor (130). In a related aspect, the vent/reservoir (140) may contain a purging fluid (e.g., $N_2$). In another aspect, the vent/reservoir (140) may allow for electro-mechanical control of fluid ingress and egress. Moreover, the vent/reservoir (140) is electrically coupled and configured to be in functional communication with the microprocessor (130). In a further aspect, one or more pumps (30), one or more valves (100), one or more monitoring devices (110), and one or more gauges (120) may be electrically coupled and configured to be in functional communication with the microprocessor (130).

The following examples are intended to illustrate but not limit the invention.

EXAMPLES

Example 1

Methods

Species-Specific PCR.

Specific amplification of the V6 region of the 16S rRNA gene was performed using PCR as disclosed by Klijn et al., Appl Env Microbiology (1995) 61(8):2919-2924. The reactions were carried out in sterile 0.5 ml tubes which contained 50 µl of the following buffer: 10 mM Tris-HCl (pH 8.8), 3.0 mM $MgCl_2$, 50 mM NaCl, 2.5 mM (each) deoxynucleotide triphosphates, 1 U of Taq polymerase, and 15 ng (each) of primers P1 5'-GCG GCG TGC CTA ATA CAT GC-3' (SEQ ID NO:1) and P2 5'-GGG TTG CGC TCG TTG CGG GA-3' (SEQ ID NO:2). After being heated to 95° C. to eliminate protease activity, 5 µl of template DNA were added (i.e., DNA extracted from cultures). Amplification was done in 30 cycles of melting DNA at 94° C. for 1 min, annealing at 55° C. for 1.5 min, and elongation at 72° C. for 2.5 min.

The resulting PCR products were diluted 10 fold, then 5 µl of this dilution was used as the template for the second PCR amplification with the P5 5'-GGA ATC TTC CAC AAT GGG CG-3' (SEQ ID NO:3), and one of the specific primers below:

```
                                         (SEQ ID NO: 4)
    Pac-A GGA CTT CAT CCA TTA CGG ACT AAC;

(SEQ ID NO: 5)
    Pbe-A CTT CCC CGA TTA AGG GTA ATT CAG;

(SEQ ID NO: 6)
    Pbu-A GTG GCT TGC TCC ATT ACA GAG TAA;
```

```
                                         (SEQ ID NO: 7)
    Pty-A CGC CTA TCT CTA GGT TAT TCA G;
or (SEQ ID NO: 8)
    Psp-A CAC CTA TCT CTA GGC TAT GCA A.
```

In the second step, the conditions were adapted with respect to annealing temperature (63° C. or 72° C.) and the number of cycles (20 or 25). When the annealing temperature was closer to the elongation temperature (i.e., 72° C.), the number of cycles was decreased.

Culture Conditions.

Anaerobic conditions are required by *C. beijerinkii*. However, brief exposures of cultures to oxygen at atmospheric concentrations are not lethal. The composition of the medium used is given in Table I.

Resazurin is an indicator of oxygen contamination; it is colorless in the absence of oxygen. All components, with the exception of concentrated sugar stocks, were mixed and sterilized by autoclaving at 121° C. for 15 mins. Sugar solutions were autoclaved separately to avoid the formation of toxic compounds and were added when the temperature of solutions had cooled to approximately 65° C. Trace minerals solution was sterilized by microfiltration (0.2 microns). The initial sugar substrate concentration was 50 g/L. Once all of the components of the medium were mixed, oxygen that may have infiltrated the solution was reduced by placing the solution under vacuum at negative 60 mm Hg until the resazurin was colorless. The head space of the vessel was then flushed with nitrogen gas. Deoxygenated medium was inoculated with an aliquot of active seed culture and incubated at 33° C. to 37° C. without agitation. Data were generated using a 400 ml working volume in the culture vessel.

Product Analysis.

Figure 2:
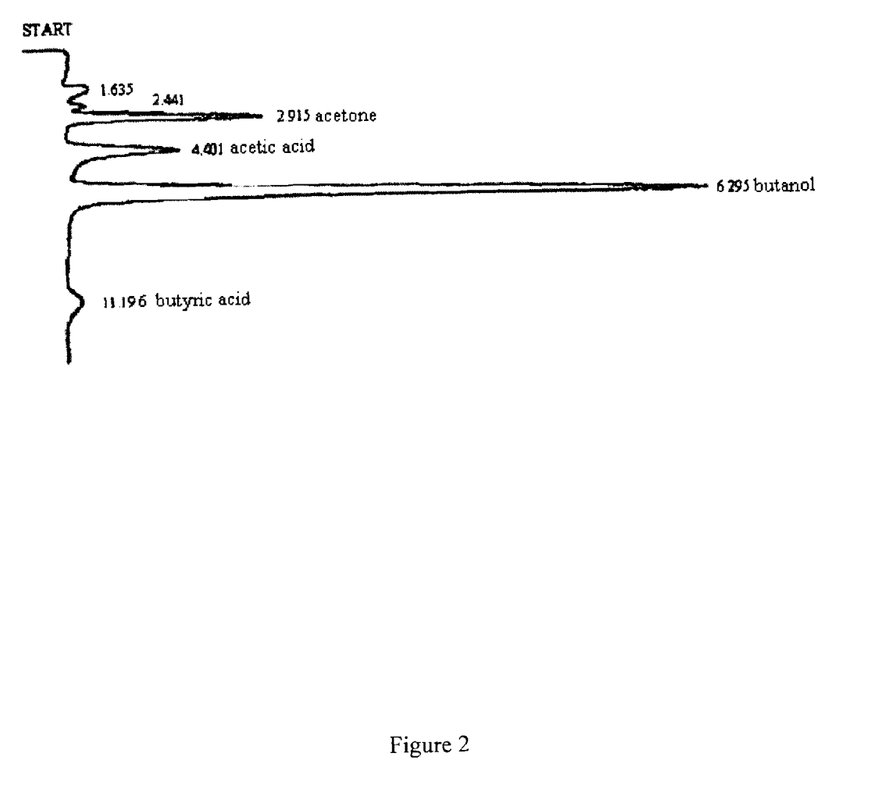
FIG. 2 shows a chromatograph of butanol produced from a *C. beijerinkii* NRRL No. B-50244 culture.

Products of fermentation were analyzed by gas chromatography (GC). A single column packed with Chromosorb-101 was sufficient to resolve all relevant fermentation products. Material eluted from the column was detected by flame ionization. Signals from the flame ionization detector were routed to an integrator for plotting and computation of peak areas. A typical chromatograph of a 1 microliter aliquot of an active culture is shown in FIG. 2. As can be seen in the figure, the major product of fermentation is butanol.

Butanol Production and Growth

In order to determine conditions for robust cell growth and butanol synthesis, cultures were grown in media as described above and aliquots taken over time were analyzed for butanol production. For the data generated in FIGS. 3 and 4, cell growth butanol production was compared between "free" cells (i.e., cells in suspension) and cells embedded in alginate beads. Alginate-bead embedding was carried-out by "gelling" droplets of alginate-supplemented cell suspensions in $CaCl_2$ solutions (100 mM). Cultures were initiated by inoculating medium with either an aliquot of an overnight "free" culture in late log phase or an aliquot of an overnight alginate bead-containing culture. Aliquots of the cell cultures were analyzed using GC as described above. A GC peak area of $5.0 \times 10^6$ units corresponds to a butanol concentration of about 1% (w/w).

Figure 3:
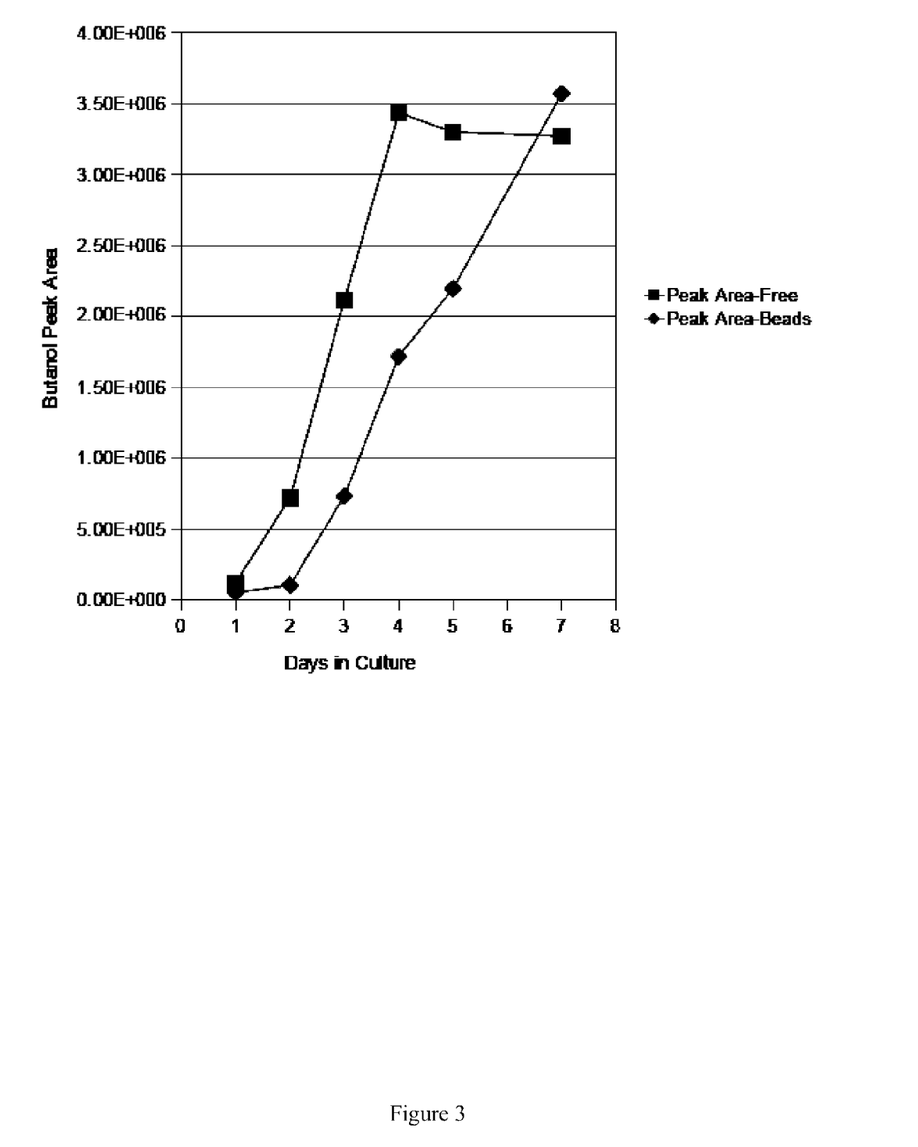
FIG. 3 graphically illustrates butanol synthesis time courses observed for free versus embedded cells. Solid squares represent data from *C. beijerinkii* cells free in culture. Solid diamonds represent data from *C. beijerinkii* cells embedded in alginate beads.
Figure 4:
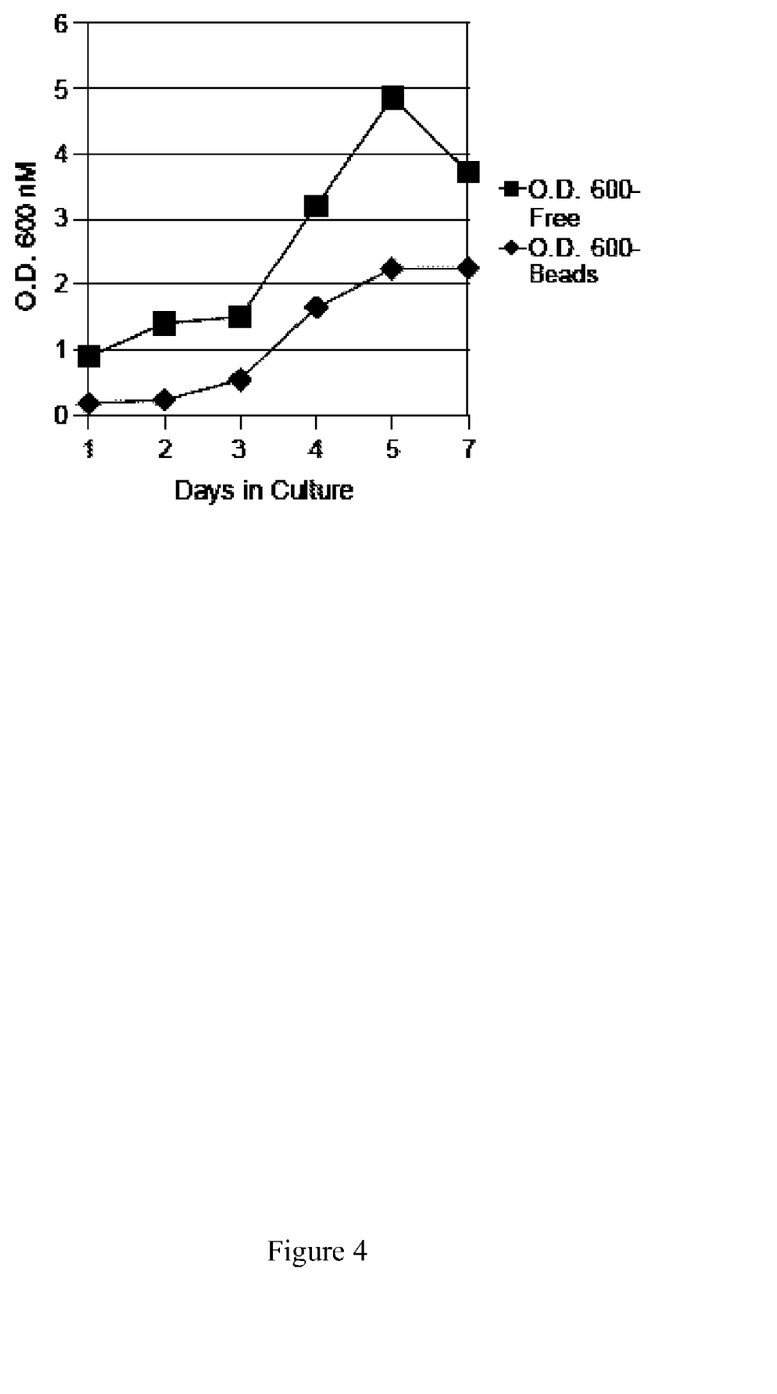
FIG. 4 graphically illustrates cell growth rates for free versus embedded cells at $OD_{600nm}$. Data points were taken in parallel with the butanol data points in FIG. 3. Solid squares represent data from *C. beijerinkii* cells free in culture. Solid diamonds represent data from *C. beijerinkii* cells embedded in alginate beads.

As can be seen in FIG. 3, for the "free" cells, butanol production increases rapidly between day 1 and day 4, with production trending downward by day 7. For the embedded cells, after a lag period of about 1 day, butanol production increased at a slightly slower rate than that of the "free" cells, however, the production was significantly higher for the embedded cells at 7 days post-inoculation.

Control of pH with Provision of "Micro-Environments."

Solvent production was robust at pH 5.0-5.5. Activity of the cultures is substantially reduced if the pH is allowed to fall to 4.5 or below. The starting pH of the weakly-buffered growth media is at pH 6.5-7.0 to foster the acidogenic phase (i.e., generation of butyric acid). The pH of the solution must be allowed to fall to trigger a shift to the solventogenic/butanol synthesis phase.

Calcium carbonate was added to prevent the culture pH from falling below 4.8-5.0. Alternatively, rather than use calcium carbonate crystals for this purpose, biological sources of calcium carbonate (e.g., cuttlebone or oyster shell fragments at approximately 10 milligrams per milliliter) can be used. Using these sources afforded, in a single vessel, the achievement of "microenvironments," and a larger "gradient of buffering capacity," in order to foster maintenance of subpopulations of acidogenic and solventogenic cells.

In addition, and in view of the results demonstrating the advantages of embedding cells in a solid phase, fragments of sponge were included in "free" cell cultures (either natural sea sponge or cellulose sponge), which fragments were colonized by the bacteria. The embedded sponge fragments were found to serve as an excellent inoculum for cultures that initiate butanol production immediately; i.e., the "sponge-bound" cells achieve rapid onset of butanol synthesis in the absence of the observed lag associated with embedded alginate-beads.

The original plan for butanol production was to extend the work of Ramey (see, e.g., U.S. Pat. No. 5,753,474) because review of the pertinent literature indicated that the system as disclosed by Ramey (i.e., the two stage, fixed bed reactor that employed *Clostridium acetobutylicum* and *C. tyrobutyricum*) could be significantly more productive than others that employed *Clostridium acetobutylicum*. A screening of *C. acetobutylicum* strains was conducted to identify one that would be most productive; it was observed that the NRRL "*C. acetobutylicum*" strain B597 had the desired characteristics. However, the B597 strain was shown to be a strain of *C. beijerinkii* (via implementation of the DNA sequence-based assay recited above). A mutant strain was isolated from B597, which strain was deposited on Feb. 12, 2009 as NRRL No. B-50244. It was shown that this purified mutant had a novel phenotype in that *C. beijerinkii* NRRL No. B-50244 was able to make butanol outside of the normal pH range which is typical for solventogenic *Clostridium* species; i.e., pH 4.8 to 5.0. In fact, the *C. beijerinkii* NRRL No. B-50244 can produce butanol at pH 6.0. As such, Ramey's two stage method was no longer applicable. Thus, for this example, butanol production was carried out with *C. beijerinkii* NRRL No. B-50244. The process as disclosed has comparable yields of butanol as Ramey's process (see Table 2), yet is much less complex in design and execution.

TABLE 2

Yield Comparison to Two Stage Method of Ramey.

| Ramey* Process Yield | | Present Process Yield |
|---|---|---|
| Theoretical | Actual | Actual |
| 38.4% | 34.9% | 40.0% |

*Based on values as disclosed in U.S. Pat. No. 5,753,474.

Example 2

Purification of Butanol from Fermentation Cultures by Vacuum Distillation

One problem with production of butanol via fermentation with C. acetobutylicum or C. beijerinkii has been the toxicity of butanol to the cells. The maximum butanol concentration that can be tolerated, irrespective of sugar concentration, is about 2% (wt/v).

A possible solution to the problem, namely, vacuum distillation of the butanol/water azeotrope was attempted. The boiling point of butanol is approximately 118° C. and the boiling point of water is 100° C. However, if a mixture of butanol and water is heated at atmospheric pressure, a low-boiling azeotropic mixture of butanol and water will evaporate at 93° C.

The vapor composition of the azeotrope is about 55.5 wt % butanol and 45.5 wt % water. The solubility of butanol in water is only 7.7 weight % so a condensate will form two layers. The upper layer is 58 mole % butanol and 42 mole % water: i.e., 80% butanol/20% water by weight. The lower layer contains 7.7% butanol by weight.

The upper layer can be burned as fuel directly, without further purification, and the lower layer contains sufficient butanol (about 1.0 M butanol) to generate usable electric current in a "methanol fuel cell" without further enrichment. Alternatively, the lower layer can be redistilled to obtain additional 80% butanol. Butanol at >99% concentration can be obtained through a "molecular sieve" as is done to obtain 100% ethanol.

Low Pressure Distillation of Butanol-Producing Cultures.

Conditions to establish azeotropic behavior in the butanol/water mixture of the fermentation broth at low temperature under reduced pressure were determined. If conditions to produce such behavior were observed, a simple and inexpensive process could be used to achieve two goals: 1) the harvesting of butanol and reduction of its concentration in the media to sub-inhibitory levels and 2) if the cells were not killed, butanol synthesis would resume when optimal conditions were re-established, where the process would be amenable to continuous production from a single fermentation vessel.

Figure 5A:
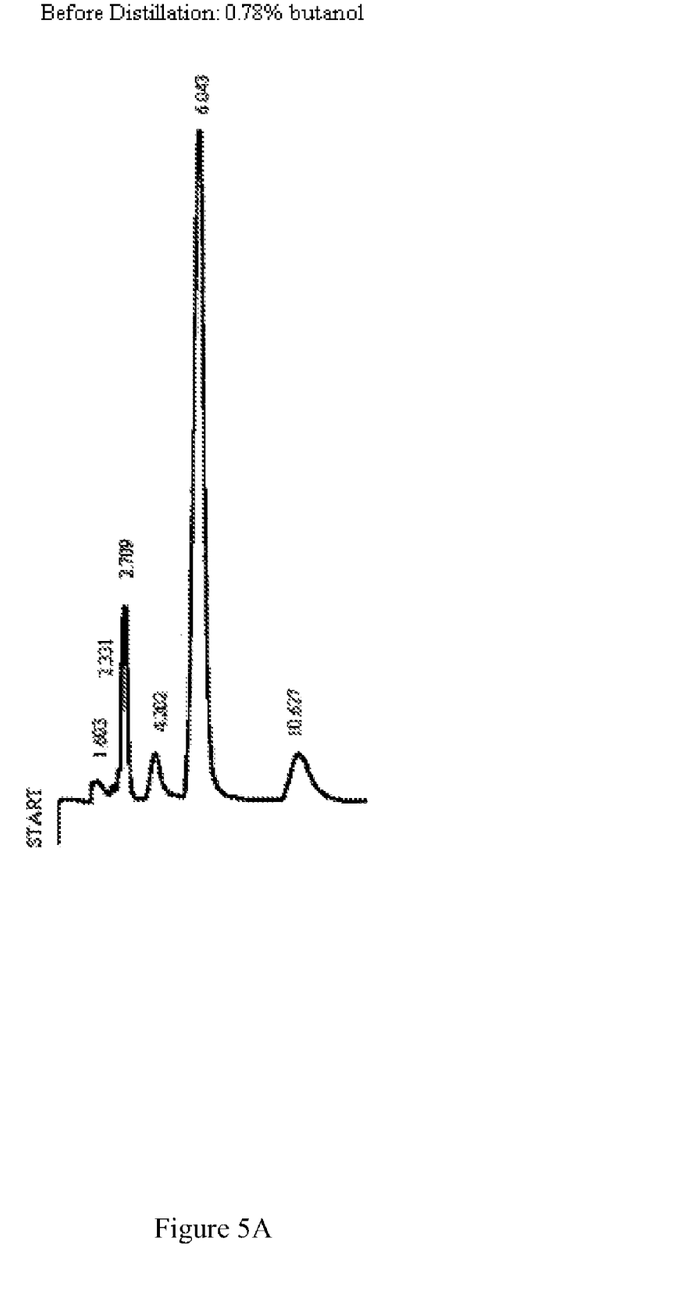
FIG. 5(A)-(C) shows a series of chromatographs demonstrating resumption of butanol synthesis subsequent to vacuum distillation. (A) Shows butanol concentration before distillation. (B) Shows butanol concentration after distillation. (C) Shows butanol concentration after re-incubation. Peaks may be keyed to FIG. 2. All % values are vol/vol.
Figure 5B:
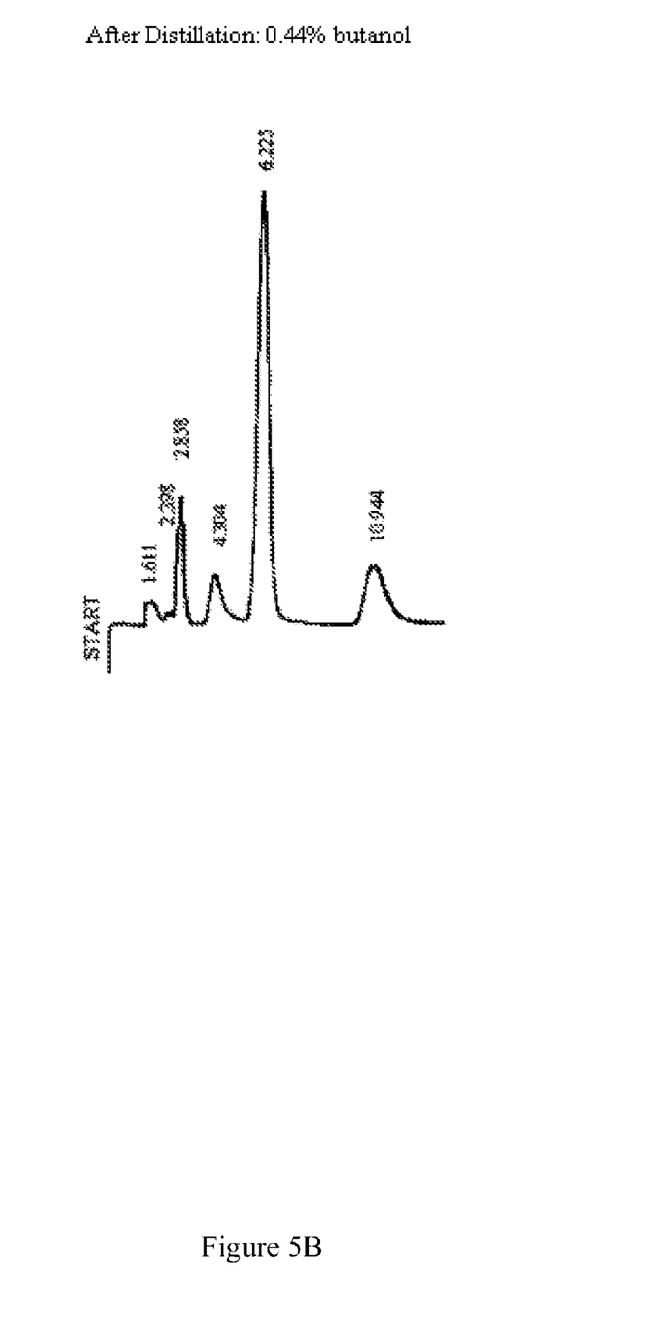

The temperature of the culture was raised to approximately 43° C. and a vacuum was applied through a condensation trap (see, e.g., (40) and (50) FIG. 1). Vigorous boiling of the culture solution commenced when the vacuum reached approximately 110 mm Hg. When the rate of collection of condensate began to decline, the culture vessel was flushed with nitrogen gas and the temperature returned to 35° C. When the yield of solvents indicated that the cells consumed the available sugar or feedstock (i.e., butanol with little acetone, see, e.g., FIG. 5(A)), more feedstock was added at that time, and feedstock volume was used to replace the volume of liquid lost to distillation.

Figure 5C:
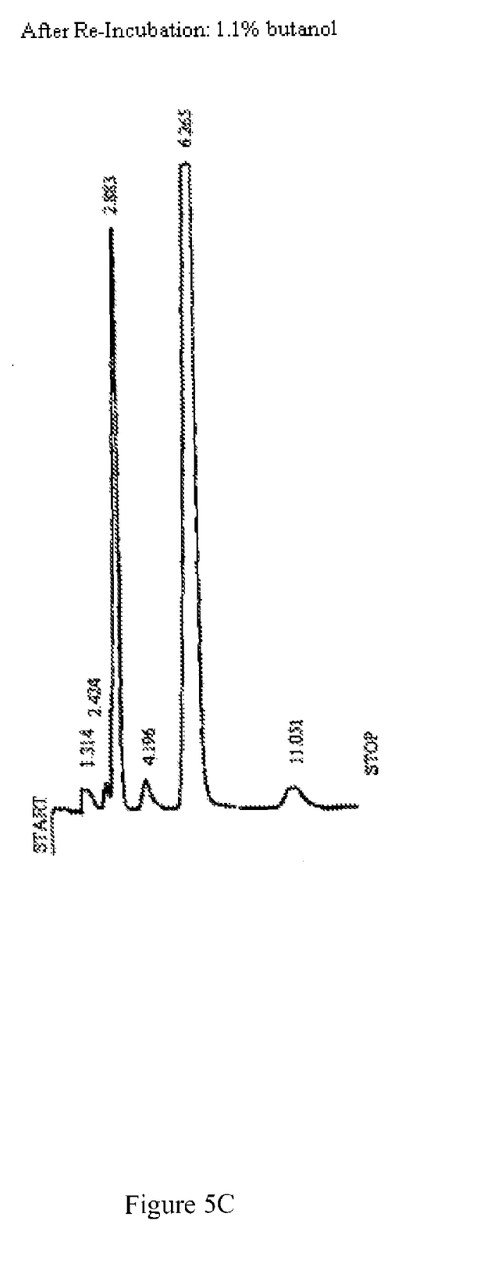

As can be seen in FIG. 5(C), butanol-inhibited cultures that were vacuum-distilled at about 43° C. and between 110 mm Hg to 100 mm Hg resume synthesis of butanol when optimal conditions were re-established.

Although the invention has been described with reference to the above examples, it will be understood that modifications and variations are encompassed within the spirit and scope of the invention.

All references cited herein are herein incorporated by reference in their entirety.

I claim herein:

1. A continuous process for the production of butanol comprising:
   (a) contacting a liquid culture of *Clostridium* cells and a buffering agent with a carbohydrate containing substrate in a first vessel;
   (b) culturing the cells at an optimum temperature for solvent production until an inhibitory concentration of butanol is attained;
   (c) decreasing the pressure in the first vessel until vigorous boiling commences;
   (d) transferring a butanol containing azeotrope from the first vessel to a second collection vessel as a condensate;
   (e) flushing the first vessel with a purging fluid; and
   (f) continuously repeating steps (b)-(e).

2. The process of claim 1, wherein flushing is a function of condensation collection volume, and wherein said flushing is initiated when the condensation collection volume is about 4% to 5% of culture volume.

3. The process of claim 1, further comprising replenishing the carbohydrate containing substrate when solvent yield is about 35% to 40% (wt/wt) of assimilable carbohydrate in the substrate.

4. The process of claim 1, wherein the culture comprises a mixture of cells in the acidogenic and solventogenic phase.

5. The process of claim 1, wherein the *Clostridium* cells are selected from the group consisting of *C. beijerinkii, C. acetobutylicum, C. aurantibutyricum, C. tetranomorphum,* and *C. thermocellum.*

6. The process of claim 1, wherein the pressure is decreased from about 760 mm Hg to about 20 mm Hg to 30 mm Hg.

7. A continuous process for the production of butanol comprising:
   (a) contacting a liquid culture of *Clostridium* cells and a buffering agent with a carbohydrate containing substrate in a first vessel;
   (b) culturing the cells at an optimum temperature until an inhibitory concentration of butanol is attained;
   (c) increasing the temperature of the culture about 6° C. to 11° C. above the optimum temperature for solvent production and decreasing the pressure in the first vessel until vigorous boiling commences;
   (d) transferring a butanol containing azeotrope from the first vessel to a second collection vessel as a condensate;
   (e) flushing the first vessel with a purging fluid and cooling the culture to the optimal temperature; and
   (f) continuously repeating steps (b)-(e).

8. The process of claim 7, wherein the optimum temperature is about 33° C. to 37° C.

9. The process of claim 8, wherein the temperature is increased to about 43° C. to 44° C. in step (c).

10. The process of claim 7, wherein flushing and cooling is a function of condensation collection volume, wherein the flushing and cooling is initiated when the condensation collection volume is about 4% to 5% of the culture volume.

11. The process of claim 7, wherein the pressure is decreased from about 760 mm Hg to about 110 mm Hg to 100 mm Hg.

12. The process of claim 7, wherein the inhibitory concentration is about 0.9% to 2.0% (w/v).

13. The process of claim 7, wherein the buffering agent comprises a biological source of calcium carbonate.

14. The process of claim 13, wherein the biological source is cuttlebone or oyster shell.

15. The process of claim 7, further comprising contacting the cells with fragments of sponge, wherein the sponge comprises calcium carbonate, silica spicules or cellulose.

16. The process of claim 7, wherein the process achieves a butanol yield of between about 35 to 40% (w/w) from fermentable carbohydrate.

17. The process of claim 7, wherein the process produces at least 0.35 grams of butanol per gram of sugar consumed.

\* \* \* \* \*